US012766301B2

(12) United States Patent
Mezzano et al.

(10) Patent No.: US 12,766,301 B2
(45) Date of Patent: Oct. 20, 2026

(54) INFUSION SITE OF A BLOOD TUBING SYSTEM

(71) Applicant: FRESENIUS MEDICAL CARE DEUTSCHLAND GMBH, Bad Homburg (DE)

(72) Inventors: Matteo Mezzano, Crema (IT); Clelia Di Caro, Milan (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 343 days.

(21) Appl. No.: 18/559,818

(22) PCT Filed: May 11, 2022

(86) PCT No.: PCT/EP2022/062729
§ 371 (c)(1),
(2) Date: Nov. 9, 2023

(87) PCT Pub. No.: WO2022/238457
PCT Pub. Date: Nov. 17, 2022

(65) Prior Publication Data
US 2024/0216666 A1 Jul. 4, 2024

(30) Foreign Application Priority Data
May 12, 2021 (EP) .................................... 21173535

(51) Int. Cl.
*A61M 39/10* (2006.01)
*A61M 1/36* (2006.01)

(52) U.S. Cl.
CPC .......... *A61M 39/105* (2013.01); *A61M 1/367* (2013.01); *A61M 1/3672* (2013.01); *A61M 1/3661* (2014.02); *A61M 2206/14* (2013.01)

(58) Field of Classification Search
CPC .... A61M 1/342; A61M 1/367; A61M 1/3672; A61M 39/105; A61M 39/10; A61M 2206/14; A61M 2206/20
See application file for complete search history.

(56) References Cited

U.S. PATENT DOCUMENTS

2014/0050614 A1 2/2014 Klewinghaus
2014/0261713 A1* 9/2014 Schriver ................ B01F 27/50 366/182.2

(Continued)

FOREIGN PATENT DOCUMENTS

EP 3 421 061 2/2019
WO 2009030973 3/2009

*Primary Examiner* — Susan S Su
(74) *Attorney, Agent, or Firm* — Kilyk & Bowersox, P.L.L.C.

(57) ABSTRACT

An infusion site for a blood tubing set, comprises a first (102) and a second (104) connection sites for connecting a first and a second tubing portion of the blood tubing set to the infusion site (100), and suitable to let a first and a second liquid enter the infusion site (100); and a third connection site (103) for connecting a third tubing portion of the blood tubing set to the infusion site (100) and suitable to let a third liquid exit the infusion site (100). The infusion site (100) further comprises a first main channel (120) in fluid communication to the first connection site (102) for conducting the first liquid through the infusion site (100); a second main channel (130) in fluid communication to the third connection site (103) for conducting the third liquid out from the infusion site (100); wherein the first main channel (120) is vertically offset to the second main channel (130) and the first main channel (120), the secondary channel (140) and the second main channel (130) are in fluid communication to each other. The infusion site (100) further comprises an inner turbulence chamber (150), located downstream from and in fluid communication to the first main channel (120)

(Continued)

and the secondary channel (140) and located upstream and in fluid communication to the second main channel (130), and comprising an inlet deflector (160) suitable to deflect the fluids entering the infusion site (100) and a re-circulator (170) suitable to recirculate the fluid inside the infusion site (100).

14 Claims, 2 Drawing Sheets

(56) References Cited

U.S. PATENT DOCUMENTS

| | | | | |
|---|---|---|---|---|
| 2020/0016314 | A1 | 1/2020 | Hacker et al. | |
| 2020/0016319 | A1 | 1/2020 | Frugier et al. | |
| 2023/0063649 | A1 * | 3/2023 | Cowan ................ | A61M 39/105 |

* cited by examiner

INFUSION SITE OF A BLOOD TUBING SYSTEM

The present invention relates to the technical field of the devices for introducing media into the body, and in particular the invention concerns an infusion site of a blood tubing system.

During an extracorporeal blood treatment, like haemodialysis, infusion solutions or medicaments are mostly infused through the extracorporeal blood circuit, i.e., the utilized blood tubing system. For example, anticoagulation infusion solutions are regularly infused in an extracorporeal blood treatment to prevent a possible occlusion of the extracorporeal blood circuit.

In a Citrate-Calcium haemodialysis treatment, blood coagulation is prevented by injecting citrate in the blood stream, as soon as the blood enters the tubing system, so reducing calcium present in the blood. After filtration and prior to returning blood to the patient, the quantity of calcium is rebalanced by injecting in the stream a predetermined quantity of calcium, since too-low calcium concentrations influence nerves and muscles, the blood coagulation and functions of lung, heart and kidneys.

This treatment requires from the tubing system two permanent infusion sites located in the arterial (citrate infusion) and the venous (calcium infusion) portion of the tubing system, as near as possible to the entrance and exit of the tubing set respectively.

To reduce coagulation processes at the calcium-infusion site into the extracorporeal blood circuit an improved mixing of blood with the infusion solution is needed. A known solution to overcome possible mixing imbalance is the creation of a localized turbulence in correspondence of the infusion site with the consequent laminar flow disruption which will increase blood and calcium mixing.

WO2009/030973 discloses a blood line comprising an infusion site intended to inject into the line a solution. The blood line comprises a first main channel having a first passage section, a second main channel having a second passage section, and a turbulence generating area including a Venturi valve which is able to improve the mixing of blood with the infusion solution.

EP3645072, of the same Applicant, discloses a double flow mixing connector on the venous line, which forces a localized turbulence by separating the inlet blood flow in two circular streams and colliding them in the calcium injection point.

Several test conducted by the Applicant have shown a need to further increase the balance between calcium infused and the blood stream, both from the hydraulic (e.g. laminar flow separation, diffusion-driven mixing between the two species) and chemical (e.g. high calcium concentration) point of view.

A general object of the present disclosure is that of providing a solution to this need. This and other objects are achieved by the embodiments of the invention having the features recited in the independent claims. The dependent claims delineate preferred and/or especially advantageous aspects.

An embodiment of the disclosure provides an infusion site for a blood tubing set, comprising,

- a first connection site for connecting a first tubing portion of the blood tubing set to the infusion site and suitable to let a first liquid enter the infusion site;
- the first connection site defining a first inlet and a first main channel in fluid communication to the first inlet for conducting the first liquid through the infusion site;

- a second connection site for connecting a second tubing portion of the blood tubing set to the infusion site and suitable to let a second liquid enter the infusion site;
- the second connection site defining a second inlet and a secondary channel in fluid communication to the second inlet for conducting the second liquid through the infusion site;
- a third connection site for connecting a third tubing portion of the blood tubing set to the infusion site and suitable to let a third liquid exit the infusion site;
- the third connection site (103) defining an outlet and a second main channel in fluid communication to the outlet for conducting the third liquid out from the infusion site;
- wherein the first main channel, the secondary channel and the second main channel are in fluid communication to each other;
- an inner turbulence chamber, located downstream from and in fluid communication to the first main channel and the secondary channel and located upstream and in fluid communication to the second main channel;

the first main channel is vertically offset to the second main channel, and the inner turbulence chamber comprises an inlet deflector suitable to deflect the fluids entering the infusion site and a re-circulator suitable to recirculate the fluid inside the infusion site.

Further advantages and characteristics of the invention shall emerge from the following description, with reference to the attached drawings, wherein.

Reference will now be made in detail to the various embodiments of the invention, of which one or more examples are illustrated in the appended figures. Each example is provided merely by way of illustration of the invention and is not intended as a limitation thereof. For example, the technical features illustrated or described being part of an embodiment may be adopted on, or in association with, other embodiments for producing a further embodiment. It is to be understood that the present invention shall be inclusive of such modifications and variants.

It is also underlined that the present description is not limited in its application to the construction and arrangement details of the components as described below using the appended figures. The present description can envisage other embodiments and be realised or implemented with other technically equivalent features. The terms used below are merely descriptive and should not be considered limiting.

Figure 1:
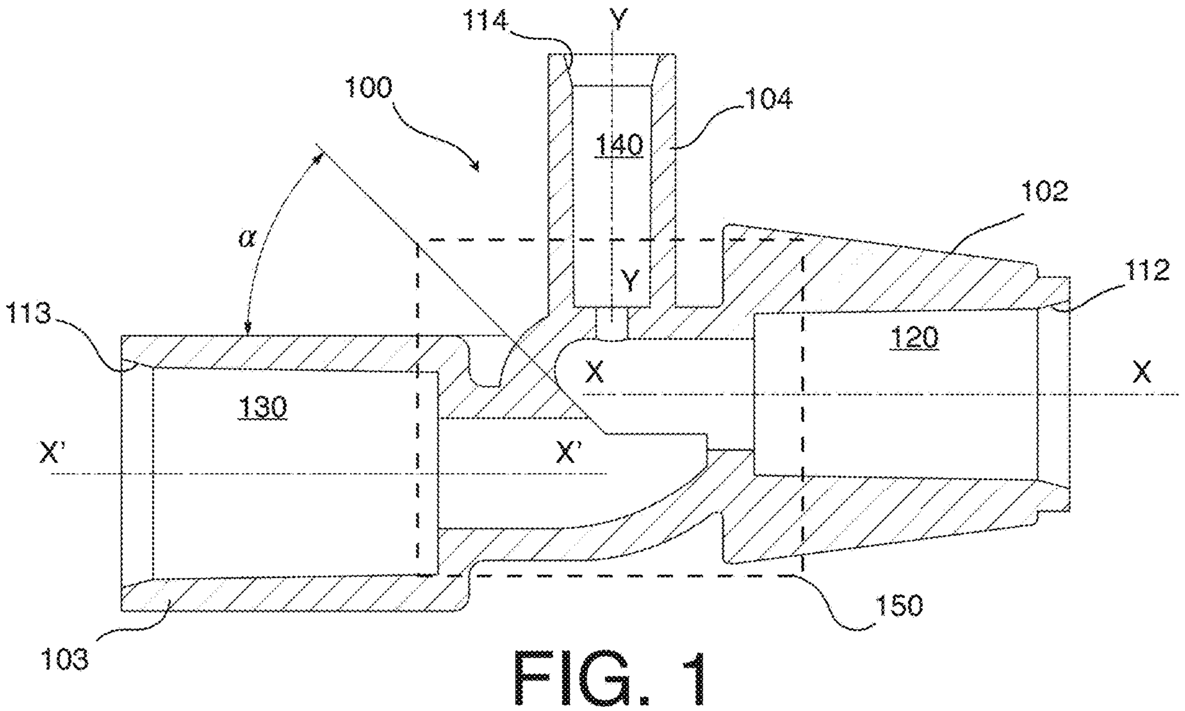
FIG. 1 shows the infusion site in a first cut in the longitudinal direction in a plan view of a first exemplary embodiment.
Figure 2:
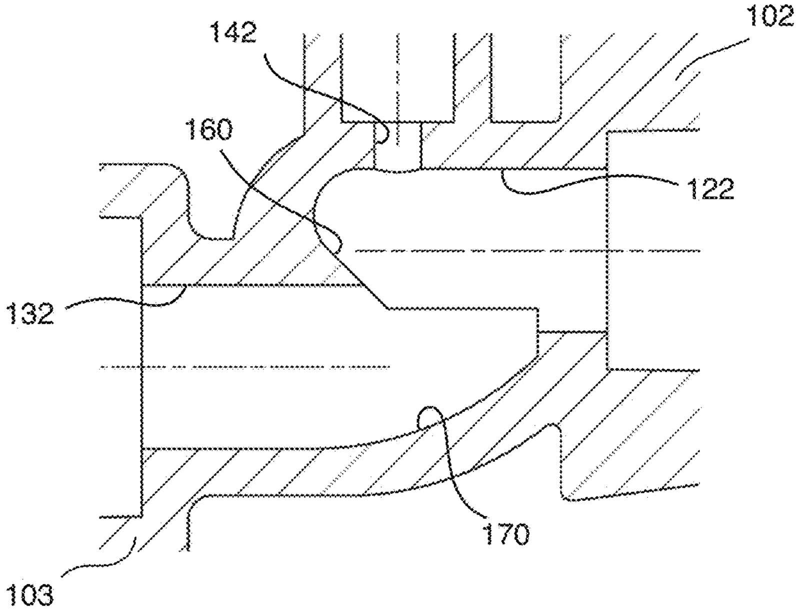
FIG. 2 shows the inner turbulence chamber of the infusion site of FIG. 1.
Figure 3:
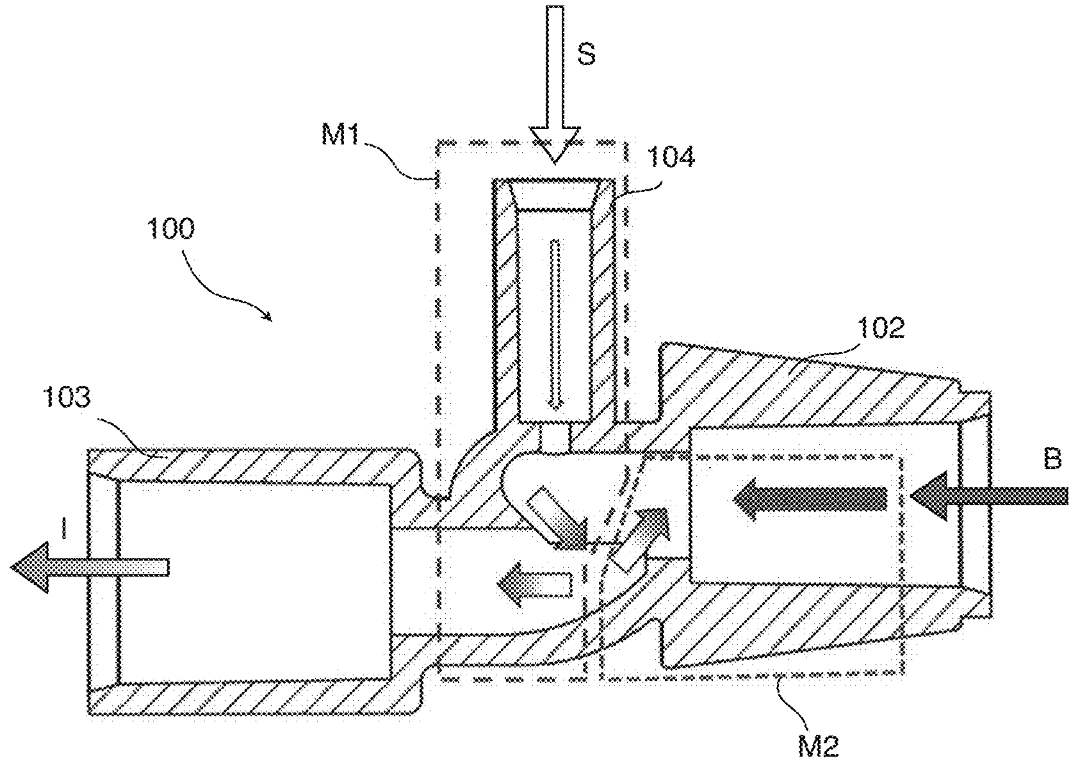
FIG. 3 shows the flow paths inside the infusion site of FIG. 1.

According to a first exemplary embodiment shown in FIG. 1, an infusion site 100 for a blood tubing set (not shown), according to the present invention, may comprise a first connection site 102 defining a first inlet 112 and a first main channel 120 elongated along a first predetermined central axe X-X, the axe X-X being in a horizontal or left-right direction in the figures.

The infusion site 100 may comprise a second connection site 104 defining a second inlet 114 and a secondary channel 140 elongated along a second predetermined central axe Y-Y, the axe Y-Y being in a vertical or top-bottom direction in the figures. The secondary channel 140 may also comprise an outlet 142 arranged opposite to the inlet 114 and facing the first main channel 120. According to one of the embodiments of the present invention, the outlet 142 may a be a narrowed section of the secondary channel 140.

The infusion site 100 may comprise a third connection site 103 defining an outlet 113 and a second main channel 130, elongated along a third predetermined central axe X'-X' which is parallel to the first predetermined axe X-X and offset thereto along the second predetermined axe Y-Y. Thus, the first main channel 120 is offset to the second main channel 130 in a vertical direction in the figures. All the three channels 120, 130 and 140 are in fluid communication to each other.

According to one of the embodiments of the present invention, the first 120 and the second 130 main channels may comprise a narrowed section 122, 132 arranged opposite to the first inlet 112 and to the outlet 113 respectively. Each of narrowed section 122, 132 has a narrowed internal circular section with respect to internal circular section of the first 120 and the second 130 main channels. Thus, the narrowed section 122 of the first main channel 120 is offset to the narrowed section 132 of second main channel 130 in a vertical direction in the figures.

In certain embodiments, the second predeterminate axe Y-Y of the secondary channel 140 may not be perpendicular to the axes X-X and X'-X' of the first 120 and the second 130 main channel respectively.

Figure 4:
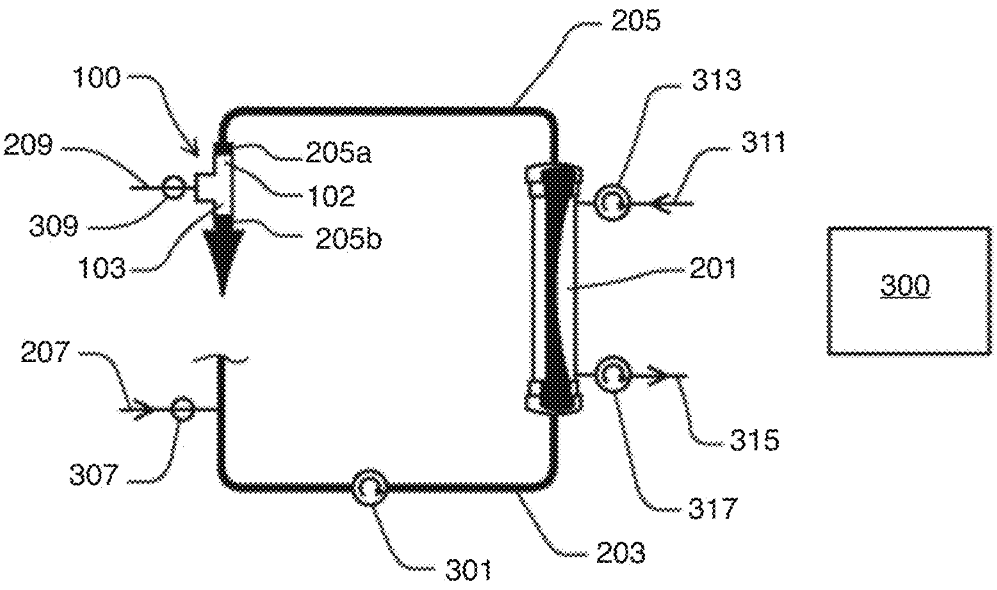
FIG. 4 shows a blood tubing set according to the present invention having an infusion site according to the present invention.

In use, the infusion site 100 acts between three tubes of a blood tubing set. FIG. 4 shows an exemplary embodiment of an optional basic arrangement of an infusion site 100 as described herein in an extracorporeal blood tubing set 200 according to the present invention, the latter being illustrated in a schematically highly simplified manner. The blood tubing set 200 comprises a hemofilter 201 or is connected thereto. A blood withdrawal line 203 (or arterial line) and a blood return line 205 (or venous line) are connected to the hemofilter 201 or dialyzer or blood filter. The blood withdrawal line 203 is operatively connected to, or comprises, a blood pump 301.

An addition line, here a line 207 for citrate solution, opens upstream of the blood pump 301 into the blood withdrawal line 203. The line 207 is operatively connected to, or comprises, a citrate pump 307.

Downstream of the hemofilter 201, a further addition line, here a line 209 for an electrolyte solution, in particular a calcium solution according to the present invention, opens into the blood return line 205. The infusion site 100 according to the present invention is operatively connected to a calcium pump 309 or comprises the latter. It is supplied by a source for infusion solution which is not shown in FIG. 4, herein exemplarily a calcium source. The source may be a bag or a bottle. The infusion solution may optionally be generated on-line; in such case the respective device, in which the infusion solution is generated, is considered as a source.

The operative connection to the calcium pump 309 is to be understood herein as an example. Arranging the infusion site 100 behind another pump than a calcium pump, i.e. for example downstream of a citrate pump like the citrate pump 307 of FIG. 4, is one of the possible embodiments of the present invention.

The hemofilter 201 is connected to a line 311 for fresh dialysis liquid and to a line 315 for spent dialysate or filtrate. The line 311 is connected to, or comprises, a dialysis liquid pump 313. The line 315 is connected to, or comprises, a filtrate pump 317.

The arrowhead indicates the flow direction when using the blood tubing set 200 as intended.

The blood tubing set 200 shown in FIG. 4 may correspond to a standard extracorporeal blood tubing set and may in particular be suitable for the CWHD (continuous veno-venous haemodialysis). The pumps 301, 307, 309, 313 and 317 may be part of a blood treatment apparatus 300 which is only schematically indicated. The same applies for the lines 311 and 315.

The first connection site 102 may be connected in fluid communication to a first tubing portion 205*a* of the blood tubing set 200, for example the blood-return line 205, so that a liquid, preferably blood, enters the infusion site 100 at the first inlet 112 conducted by the first main channel 120 in the direction of the arrow B.

The second connection site 104 may be connected in fluid communication to a tubing portion of the line for calcium solution 209, so that an infusion solution, enters the infusion site 100 at the second inlet 114 conducted by the secondary channel 140 in the direction of the arrow S, and enter into the first main channel 120 through the outlet 142. The infusion solution may be a liquid comprising a calcium-substitution solution, or any other type of solution used in haemodialysis treatment, or even a medicament.

The third connection site 103 may be connected in fluid communication to a second tubing portion 205*b* of the blood tubing set 200, for example the blood return line 205, so that a third liquid, preferably the infusion of blood and infusion solution, exits the infusion site 100 at the outlet 113 conducted by the third main channel 130 in the direction of the arrow I.

The infusion site 100 comprises an inlet deflector 160 suitable to deflect the fluids entering the infusion site 100. In particular, the inlet deflector comprises an inclined wall 160 of the first main channel 120. More particularly, the inclined wall 160 is obtained at an end of the narrowed section 122 of the first main channel 120 opposite to the first connection site 102 and facing the narrowed section 132 of the second main channel 130.

According to this configuration, the inclined wall 160 is positioned at and faced to the outlet 142 of the secondary channel 140.

The infusion site 100 further comprises a re-circulator 170 suitable to recirculate the fluid inside the infusion site 100. In particular, the re-circulator comprises a curved wall 170 of the second main channel 130. More particularly, the curved wall 170 is obtained at an end of the narrowed section 132 of the second main channel 130 opposite to the third connection site 103 and facing the narrowed section 122 of the first main channel 120.

The term "inclined wall" is used herein to indicate a surface defining a plane which forms with the first axe X-X of the first main channel 120 an angle $\alpha$ comprised between 40° and 90°. The term "curved wall" is used therein to indicate a curved surface wherein the tangent plane to the curved surface defines a plane which forms with the second axe X'-X' of the second main channel 130 an angle different from zero. According to the embodiments shown in the figures, the "curved wall" defines a concavity. Different embodiments of the present invention may comprise a different combination of inclined and curved walls for the inlet deflector 160 and the re-circulator 170.

For example, the value of the angle $\alpha$ of the inclined wall 160 is preferably comprised between 45° and 90°. The distance between the first predetermined central axe X-X and the third predetermined central axe X'-X', i.e. the offset between the first main channel 130 and the second main channel 130, is preferably comprised between 1 and 2.5 mm. The radius of the curved surface 170 is preferably comprised between 2° and 10°.

The infusion site 100 comprises an inner turbulence chamber 150, located downstream from and in fluid communication to the first main channel 120 and with the secondary channel 140, and located upstream from and in fluid communication to the second main channel 130. According to the flow path of the liquids inside the infusion site 100, the inner turbulence chamber 150 is thus defined by the narrowed section 122 arranged downstream of the inlet 112 of the first main channel 120, by the inclined wall 160 arranged downstream the narrowed section 122, by the curved wall 170 arranged downstream the inclined wall 160, and by the narrowed section 132 of the second main channel 130 arranged downstream the curved wall 170. The outlet 142 of the secondary channel 140 is arranged at and faces the inner turbulence chamber 150.

In use, a first liquid, preferably blood, enters the inner turbulence chamber 150 coming from the first connection site 102 conducted by the first main channel 120 in the direction of the arrow B.

A second liquid, preferably an infusion solution, enters the inner turbulence chamber 150 coming from the second connection site 104 conducted by the secondary channel 140 in the direction of the arrow S.

The blood entered from the first connection site 102 enters the narrowed section 122 of the first main channel 120 and encounters the inlet deflector 160, which acts as an obstacle to the stream of blood disrupting the fluid vein and allowing a pre-mixing of blood with the infusion solution coming from the inlet 142 of the secondary channel 140 and generating a premixed flow.

The premixed flow is then deflected according to the inclination of the inclined wall 160 towards the curved wall 170 of the narrowed section 132 of the second main channel 130. Reaching the curved wall 170, part of the premixed flow is redirected to the narrowed section 122 of the first main channel 120 and part of the premixed flow is discharged towards the second main channel 130.

The part of the premixed flow redirected to the narrowed section 122 of the first main channel 120 is mixed with blood which enters the first connection site 102 and that is not yet mixed with the infusion solution. Then, the premixed blood mixed with the blood encounters the inlet deflector 160 and the inlet 142 of the secondary channel 140 allowing a new mixing cycle begin.

According to the previous configuration, two mixing area inside the inner turbulence chamber 150 can be identified:

- a first mixing area M1, where the blood coming from the first connection site 102 is mixed with the infusion solution in correspondence of the deflector wall 160; and
- a second mixing area M2, where the premixed blood coming from re-circulator 170 is mixed with the blood coming from the first connection site 102.

The inclined wall 160 and the curved wall 170 allow the creation of a vortex that recirculates the premixed blood into blood entering the infusion site 100. The offset between the first 120 and the second 130 main channels permits the integration of the inclined wall 160 and the curved wall 170 in the inner turbulence chamber 150, creating a space where the vortex can develop.

Moreover, thank to this configuration, the inlet 142 of the infusion solution is positioned at the edge of the vortex, so that the infusion solution hits the blood vortex at the point of highest velocity and the mixing of the infusion solution and the premixed blood is optimized.

Experimental Results

Several tests conducted by the Applicant has shown how the present invention definitively increases the mixing capability of an infusion site of a blood tubing system. Some of the results of these tests are herein below provided merely by way of examples of embodiments of the invention and they are not intended as a limitation thereof.

Some prototypes of the present invention have been produced, with different parametric values of the single components thereof.

Internal geometry quotes were optimized with a Design of Experiment where each test was a CFD (Computational Fluid Dynamics) simulation, and where the influence of each parameter on the mixing efficiency was considered. A set of critical parameter, intended as the parameter with a statistical effect on the response, was identified and their value was set in correspondence of the highest response.

The transfer function of the optimized design was also computed and can directly links changes in the critical parameters to a change in response.

For the purpose of this design development, mixing efficiency was defined as $$\gamma = 1 - \frac{1}{2}\sum_{i=1}^{n}\left(\frac{A_i\,|wf_i - \overline{wf}|}{A\overline{wf}}\right)$$

computed on a cross section of the tube on the outside of the component, where:

$wf_i$ is the calcium volume fraction on the i-th cell of the cross section;

$\overline{wf}$ is the average calcium volume fraction on the cross section;

$A_i$ is the area of the i-th cell of the cross section;

A is the total area of the cross section;

n is the number of cells on the cross section.

Mixing efficiency gamma moves from 0 to 1, where 0 correspond to no mixing and 1 correspond to complete mixing.

The present invention has been also analysed with a computational fluid dynamic simulation at different blood and calcium feed flow condition and for different distances from the outlet of the component. Results where then used with an ANOVA (ANalysis Of VAriation) calculation to establish a relationship between mixing efficiency and blood feed rate, calcium feed rate and distance from the component.

Results from CFD and ANOVA computation showed that for predetermined flow rates range, moving along distances from the infusion site to the patient reinfusion site, the mixing efficiency is always above 0.7.

An empirical relationship can be established between the distance from the infusion site (L), the blood flow rate (Q blood) and the $\gamma$ mixing efficiency, while the calcium flow rate appeared to be not statistically significant after the ANOVA analysis.

A similar comparative CFD analysis has been performed for a standard T Hep connector and for the connector of the present invention. The results were retrieved at a two different distances (L) from the infusion site and showed that the mixing efficiency of the present invention is always above compared to the efficiency of the other one. Table 1 shows the result of the test comparison.

TABLE 1

| Connector | Distance: 0 mm Blood: 200 ml/min Calcium: 100 ml/hr | Distance: 70 mm Blood: 200 ml/min Calcium: 100 ml/hr |
|---|---|---|
| T Hep | 0.27 | 0.56 |
| the present invention | 0.70 | 0.98 |

In addition to the increased mixing capability, the test results showed that the present invention provides several advantages. The infusion site can be produced in PVC and can be easily integrated in a bloodline using current gluing technique. The present invention can be easily moulded with no impact on the actual production processes and with lower costs. The present invention has the same encumbrance as current designs, and, thus, it has no impact on an assembly procedure. The present invention can be produced as one-piece component.

The invention claimed is:

1. An infusion site for a blood tubing set, comprising:
a first connection site for connecting a first tubing portion of the blood tubing set to the infusion site and suitable to let a first liquid enter the infusion site, the first connection site defining a first inlet and a first main channel in fluid communication to the first inlet for conducting the first liquid through the infusion site;
a second connection site for connecting a second tubing portion of the blood tubing set to the infusion site and suitable to let a second liquid enter the infusion site, the second connection site defining a second inlet and a secondary channel in fluid communication to the second inlet for conducting the second liquid through the infusion site;
a third connection site for connecting a third tubing portion of the blood tubing set to the infusion site and suitable to let a third liquid exit the infusion site, the third connection site defining an outlet and a second main channel in fluid communication to the outlet for conducting the third liquid out from the infusion site; and
an inner turbulence chamber, wherein
the first main channel, the secondary channel and the second main channel are in fluid communication to each other,
the inner turbulence chamber is located downstream from and in fluid communication to the first main channel and the secondary channel and located upstream and in fluid communication to the second main channel, the first main channel is vertically offset to the second main channel, and the inner turbulence chamber comprises an inlet deflector suitable to deflect the fluids entering the infusion site and a re-circulator suitable to recirculate the fluid inside the infusion site, and
the inlet deflector comprises an inclined wall or a curved wall arranged at an end of the first main channel, which is opposite to the first inlet.

2. An infusion site according to claim 1, wherein the secondary channel comprises an outlet arranged opposite to the inlet and facing the first main channel, the inlet deflector being positioned at and faced to the outlet of the secondary channel.

3. An infusion site according to claim 1, wherein the first main channel is elongated along a first predetermined central axis, the secondary channel is elongated along a second predetermined central axis, the second main channel is elongated along a third predetermined central axis that is parallel to the first predetermined axis and offset thereto along the second predetermined central axis.

4. An infusion site according to claim 1, wherein the inclined wall defines a plane that forms, with the first axis of the first main channel, an angle of between 45° and 90°.

5. An infusion site according to claim 1, wherein the re-circulator comprises a curved wall or an inclined wall obtained at an end of the second main channel, which is opposite to the outlet.

6. An infusion site according to claim 5, wherein the second main channel comprises a narrowed section arranged opposite to the outlet and the curved wall or the inclined wall of the re-circulator is arranged at an end of the narrowed section of the second main channel.

7. An infusion site according to claim 1, wherein the first main channel comprises a narrowed section arranged opposite to the first inlet and the inclined wall or the curved wall of the inlet deflector is arranged at an end of the narrowed section of the first main channel.

8. A blood tubing set comprising at least one infusion site according to claim 1, wherein the infusion site is connected in fluid communication to an addition line and to a blood withdrawal line and/or to a blood return line.

9. The blood tubing set according to claim 8, in fluid communication with an anticoagulation infusion solution and configured for executing a regional anticoagulation.

10. The blood tubing set according to claim 8, wherein the blood tubing set is connected to a blood treatment apparatus that is configured for executing a hemodialysis, a hemofiltration, a hemodiafiltration, a plasmapheresis treatment or a whole blood adsorption treatment.

11. The blood tubing set according to claim 8, wherein the first connection site and the third connection site are connected to a blood-return line of the blood tubing set, and wherein the second connection site is connected to a line that is in fluid communication with an electrolyte solution comprising a calcium solution.

12. A blood treatment apparatus connected to the blood tubing set according to claim 8.

13. An infusion site for a blood tubing set, comprising:
a first connection site for connecting a first tubing portion of the blood tubing set to the infusion site and suitable to let a first liquid enter the infusion site, the first connection site defining a first inlet and a first main channel in fluid communication to the first inlet for conducting the first liquid through the infusion site;
a second connection site for connecting a second tubing portion of the blood tubing set to the infusion site and suitable to let a second liquid enter the infusion site, the second connection site defining a second inlet and a secondary channel in fluid communication to the second inlet for conducting the second liquid through the infusion site;
a third connection site for connecting a third tubing portion of the blood tubing set to the infusion site and suitable to let a third liquid exit the infusion site, the third connection site defining an outlet and a second main channel in fluid communication to the outlet for conducting the third liquid out from the infusion site; and
an inner turbulence chamber, wherein
the first main channel, the secondary channel and the second main channel are in fluid communication to each other, the inner turbulence chamber is located downstream from and in fluid communication to the first main channel and the secondary channel and located upstream and in fluid communication to the second main channel, the first main channel is vertically offset to the second main channel, the inner turbulence chamber comprises an inlet deflector suitable to deflect the fluids entering the infusion site and a re-circulator suitable to recirculate the fluid inside the infusion site, the re-circulator comprises a curved wall or an inclined wall obtained at an end of the second main channel, which is opposite to the outlet, and the curved wall has a degree of curvature of between 2° and 10°.

14. An infusion site for a blood tubing set, comprising:

a first connection site for connecting a first tubing portion of the blood tubing set to the infusion site and suitable to let a first liquid enter the infusion site, the first connection site defining a first inlet and a first main channel in fluid communication to the first inlet for conducting the first liquid through the infusion site;

a second connection site for connecting a second tubing portion of the blood tubing set to the infusion site and suitable to let a second liquid enter the infusion site, the second connection site defining a second inlet and a secondary channel in fluid communication to the second inlet for conducting the second liquid through the infusion site;

a third connection site for connecting a third tubing portion of the blood tubing set to the infusion site and suitable to let a third liquid exit the infusion site, the third connection site defining an outlet and a second main channel in fluid communication to the outlet for conducting the third liquid out from the infusion site; and an inner turbulence chamber, wherein the first main channel, the secondary channel, and the second main channel are in fluid communication to each other, the inner turbulence chamber is located downstream from and in fluid communication to the first main channel and the secondary channel and located upstream and in fluid communication to the second main channel, the first main channel is vertically offset to the second main channel, the inner turbulence chamber comprises an inlet deflector suitable to deflect the fluids entering the infusion site and a re-circulator suitable to recirculate the fluid inside the infusion site, the inlet deflector is an inclined wall or a curved wall arranged at the end of the first main channel opposite to the first inlet, the re-circulator is a curved wall or an inclined wall arranged at the end of the second main channel opposite to the outlet, the first main channel comprises a narrowed section arranged opposite to the first inlet and the inclined wall or curved wall of the inlet deflector is arranged at an end of the narrowed section, the second main channel comprises a narrowed section arranged opposite to the outlet and the curved wall or inclined wall of the re-circulator is arranged at an end of the narrowed section, and the inner turbulence chamber is defined by the narrowed section of the first main channel, by the inclined wall or curved wall of the inlet deflector arranged downstream of the narrowed section, and by the curved wall or inclined wall of the re-circulator arranged downstream of the inclined wall or curved wall of the inlet deflector.

* * * * *